United States Patent
Sinha et al.

(10) Patent No.: US 6,989,467 B2
(45) Date of Patent: Jan. 24, 2006

(54) MICROWAVE INDUCED PROCESS FOR THE PREPARATION OF SUBSTITUTED 4-VINYLPHENOLS

(75) Inventors: Arun Kumar Sinha, Himachal Pradesh (IN); Bhupendra Prasad Joshi, Himachal Pradesh (IN); Anuj Sharma, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 280 days.

(21) Appl. No.: 10/383,253

(22) Filed: Mar. 7, 2003

(65) Prior Publication Data

US 2004/0118673 A1     Jun. 24, 2004

(30) Foreign Application Priority Data

Dec. 19, 2002   (WO) ............... PCT/IB 02/05513

(51) Int. Cl.
*C07C 39/06*     (2006.01)

(52) U.S. Cl. .............. 568/780; 204/157.9; 204/157.92; 568/651

(58) Field of Classification Search ............... 568/780, 568/651; 204/157.9, 157.92
See application file for complete search history.

(56) References Cited

U.S. PATENT DOCUMENTS

| | | | |
|---|---|---|---|
| 4,316,995 A | 2/1982 | Pittet et al. | |
| 4,868,256 A | 9/1989 | Aslam et al. | |
| 4,868,257 A | 9/1989 | Aslam et al. | |
| 4,933,495 A | 6/1990 | Aslam et al. | |
| 5,072,025 A | 12/1991 | Vicari et al. | |
| 5,087,772 A | 2/1992 | Sheehan et al. | |
| 5,128,253 A | 7/1992 | Labuda et al. | |
| 5,247,124 A | 9/1993 | Aslam et al. | |
| 5,256,809 A | 10/1993 | Kvakoyszky et al. | |
| 5,344,963 A | 9/1994 | Warm et al. | |
| 5,493,062 A | 2/1996 | Sounik et al. | |
| 5,563,289 A | 10/1996 | Sounik et al. | |
| 6,111,133 A | 8/2000 | Houlihan | |
| 6,235,507 B1 | 5/2001 | Muheim et al. | |
| 6,468,566 B2 | 10/2002 | Ago et al. | |

*Primary Examiner*—Michael L. Shippen
(74) *Attorney, Agent, or Firm*—Foley & Lardner LLP

(57) ABSTRACT

The present invention relates to "a microwave induced process for the preparation of 4-vinylphenols or its derivatives" in which commercially important FEMA GRAS approved perfumery and flavouring vinylphenols (i.e. hydroxystyrenes) namely 4-vinylguaiacol (FEMA GRAS No. 2675) and 4-vinylphenol (FEMA GRAS No. 3739) as well as other useful vinylphenols such as 2,6-dimethoxy-4-vinylphenol, 2-hydroxy-4-vinylphenol, 3-hydroxy-4-vinylphenol etc. by condensation of malonic acid and 4-hydroxyphenylaldehydes or its derivatives.

12 Claims, 3 Drawing Sheets

$^1$H NMR (300 MHz) spectra of 4-Vinylguaiacol in CDCl$_3$

13C-NMR (75.4 MHz) spectra of 4-Vinylguaiacol in CDCl3

DEPT-135 NMR spectra of 4-Vinylguaiacol in CDCl₃

MICROWAVE INDUCED PROCESS FOR THE PREPARATION OF SUBSTITUTED 4-VINYLPHENOLS

TECHNICAL FIELD

The present invention relates to "A microwave induced process for the preparation of substituted 4-vinylphenols" in which commercially important FEMA GRAS approved perfumery and flavouring vinylphenols (i.e. hydroxystyrenes) namely 4-vinylguaiacol (FEMA GRAS No. 2675) and 4-vinylphenol (FEMA GRAS No. 3739) as well as other useful vinylphenols such as 2,6-dimethoxy-4-vinylphenol, 2-hydroxy-4-vinylphenol, 3-hydroxy-4-vinylphenol etc. are obtained in a one pot during condensation of malonic acid and corresponding substituted 4-hydroxy phenylaldehydes (4-hydroxy benzaldehydes) under microwave irradiation.

In the present invention, the formation of substituted vinylphenols is the first example from 4-hydroxy phenylaldehydes in one step under microwave irradiation otherwise literature till today reveals the formation of vinylphenols only by decarboxylation of cinnamic acid either by microorganisms or conventional methods.

BACKGROUND ART

Aroma compounds of natural origin are of major interest to flavour and fragrance industries, however, nature alone cannot meet the ever-increasing world demand on its own due to limited percentage of such compounds in plant kingdom. Therefore, there is a growing interest in developing alternative sources for natural aroma compounds and in particular, substituted 4-vinylphenols such as 4-vinylguaiacol (p-vinylguaiacol or 2-methoxy-4-vinylphenol or 4-hydroxy-3-methoxystyrene or 4-ethenyl-2-methoxyphenol), 4-hydroxystyrene (p-vinylphenol or 4-ethenylphenol), 3,5-dimethoxy-4-hydroxy styrene and others have been the most extensively investigated ones due to their widespread applications in food and alcoholic beverages, flavouring substances and as intermediates in the preparation of polymers and copolymers useful in coatings, electronic applications, ion exchange resins and photo resists etc. (Perfume and Flavor Chemicals, Aroma Chemicals, ed. Steffen, A., Allured Publishing Corporation. Vol I–IV (1994) and Encyclopedia of Food and Color Additives, ed. George, A. B., CRC Press, Inc., Vol I–II (1996)). The preparation of these substituted 4-vinylphenols such as 4-vinylguaiacol (FEMA GRAS No. 2675), 4-vinylphenol (FEMA GRAS No. 3739) and others are well known in the art, however, a more efficient process for preparing substituted 4-vinylphenols is desired and needed. The present invention provides a process wherein microwave assisted (Bose, A. K., Banik, B. K., Lavlinskaia, N., Jayaraman, M. and Manhas, M. S., Chemtech, 27, 18–24, (1997) and Larhed, M. and Hallberg, Drug Discovery Today, 6(8), 406–416, (2001)) condensation of substituted 4-hydroxy phenylaldehydes and malonic acid in the presence of organic base and organic acid provides only substituted 4-vinylphenols in one pot within 20 minutes and not cinnamic acid as generally obtained in conventional Knoevenagel-Doebner condensation reaction (Furniss, B. S., Hannaford, A. J., Rogers, V., Smith, P. W. G. and Tatchell, A. R: In: Vogel's Textbook of Practical Organic Chemistry, fourth Edn., ELBS, UK, 802 (1978); Susanne, R. H., Kerry, C. A., Dac, D. M., Ducan, J. N., Christopher, H. L., Rita, H. M., Mary, L. E., Nanette, N. F., Martin, S. W., Kjell, S. A., Matt, Z. J., Arvid, C. and Chiu-Hong, L., J. Med. Chem., 44, 4716–4732 (2001) and James, M., Jennifer, A. S. and Sonja, W., Tetrahedron Letters, 39, 8013–8016 (1998)). It is worthwhile to mention that microwave-assisted chemical transformation is a new emerging technique which is generally known for ecofriendly, rapid and high yielding process, however, such a surprising effect of microwave is observed for the first time in the above invention where both condensation and decarboxylation have occurred simultaneously without addition of decarboxylating agent.

The following prior art references are disclosed as below:
U.S. Pat. No. 6,468,566 discloses a method for the preparation of 4-vinylguaiacol from ferulic acid decarboxylase enzyme.

U.S. Pat. No. 6,235,507 disclose a method for the preparation of 4-vinylguaiacol from microbial conversion of ferulic acid at a pH more than 9.

U.S. Pat. No. 5,493,062 disclose a method for the preparation of 4-vinylphenol from p-alpha-aminoethylphenol (AEP) at high temperature.

U.S. Pat. No. 5,087,772 discloses a method for the preparation of 4-vinylphenol from 4-acetoxystyrene with a suitable alcohol in the presence of a suitable base.

U.S. Pat. No. 5,256,809 discloses a method for the preparation of 4-vinylphenol from 4-acetoxystyrene.

Journal of Biotechnology, (2000), 80, 195–202, discloses a method for the preparation of 4-vinylguaiacol from decarboxylation of ferulic acid by *Bacillus coagulans*.

Enzyme and Microbial Technology, (1998), 23, 261–266, discloses a method for the preparation of 4-vinylguaiacol from decarboxylation of ferulic acid by *Bacillus pumilus*.

Archives of Biochemistry and Biophysics, (1998), 359(2), 225–230, discloses a method for the preparation of 4-vinylphenol from decarboxylation of hydroxycinnamic acid by *Klebsiella oxytoca*.

J. Fermentation and Bioengineering, (1996), 82(1), 46–50, discloses a method for the isolation of 4-vinylguaiacol from distilled and stored model solutions of "shochu" (a name of alcoholic beverage in Japan).

Encyclopedia of Food and Color Additives, ed. George, A. B., CRC Press, Inc., Vol II, 1705 (1996) discloses a method for the preparation of styrene by reaction of phenylaldehydes with acetic anhydride in the presence of sodium acetate to give cinnamic acid followed by decarboxylation of cinnamic acid.

Perfume and Flavor Chemicals (Aroma Chemicals), ed. Steffen, A., Allured Publishing Corporation, Vol II, 1891 (1994) discloses a method for the preparation of vinylphenol (4-hydroxy-3-methoxystyrene) by catalytic oxidation of 1,1-diphenylethane (1,1-di-(4-hydroxy-3-methoxy)phenylethane).

Journal of Biol. Chem., (1993), 268, 23954–23958, discloses a method for the preparation of 4-vinylguaiacol from decarboxylation of ferulic acid by *Rhodotorula rubra*.

Appl. Environ. Microbial., (1993), 59, 2244–2250, discloses a method for the preparation of 4-vinylguaiacol from decarboxylation of ferulic acid by *Saccharomyces cerevisiae* and *Pseudomonas fluorescens*.

Journal of Biol. Chem., (1962), 237, 2926–2931, discloses a method for the preparation of 4-vinylphenol from decarboxylation of 4-hydroxy-cinnamic acid by Aerobacter.

Journal of Biol. Chem., (1961), 236, 2302, discloses a method for the decarboxylation of trans-cinnamic acids into styrene derivatives by using pyruvate decarboxylase enzyme.

Journal of Biol. Chem., (1957), 227, 151, discloses a method for the decarboxylation of trans-cinnamic acids into styrene derivatives by using oxalate decarboxylase enzyme.

Journal of Biol. Chem., (1960), 235, 1649, discloses a method for the decarboxylation of trans-cinnamic acids into styrene derivatives by using glutamate decarboxylase enzyme.

Journal of Biol. Chem., (1957), 226, 703, discloses a method for the decarboxylation of trans-cinnamic acids into styrene derivatives by using aconitate decarboxylase enzyme.

Journal of Biol. Chem., (1964), 239, 879, discloses a method for the decarboxylation of trans-cinnamic acids into styrene derivatives by using aspartate 4-decarboxylase enzyme.

Tetrahedron Letters, (1999), 40, 6595–6598, discloses a method for the decarboxylation of trans-cinnamic acids into styrene derivatives by using plant cell cultures. Journal of Biol. Chem., (1962), 237, 2926–2931, discloses a method for the decarboxylation of trans-4-hydroxycinnamic acid into 4-hydroxystyrene.

Applied Catalyst A: General, (1995), 133, 219–239, discloses a method for the preparation of styrene from dehydrogenation of ethylbenzene.

Organic Synthesis Collective Volume I, 441–442 (1941) as well as Volume IV, 731–734 (1963), discloses a method for the preparation of styrenes by decarboxylation of cinnamic acids with quinoline in the presence of copper powder at 200–300° C. Some of other typical prior art references include U.S. Pat. Nos. 4,316,995; 4,868,256; 4,868,257; 4,933,495; 5,072,025; 5,128,253; 5,247,124; 5,344,963; 5,563,289; 6,111,133; European Pat. Nos. 0-128-984; 0-108-624; Dutch Pat. Nos. 72.09426; 72.13842; 75.04532; Japan Pat. Nos. 10306126; 6049137; J. Am. Chem. Soc., 70, 2295, (1948); J. Am. Chem. Soc., 72, 5198 (1950); J. Am. Chem. Soc., 80, 3645 (1958); J. Org. Chem., 23, 544–549 (1958); Chem. Berichte, 92, 2958–2961 (1959): Tetrahedron, 31, 235 (1975); Can. J. Chem., 63, 153 (1985). Although, the above methods have been proven to be useful, they suffer from one or more process deficiencies. For example, in some instances processes of this type necessarily involve resort to sub-ambient temperatures, which of course, involves some considerable process control and lead to reaction mixtures.

It, therefore, becomes an object of the invention to provide rapid and economical process for the preparation of substituted 4-vinylphenols from cheaper and commercially available 4-hydroxy phenylaldehydes as well as to eliminate the disadvantages associated with the above patents and papers.

In conclusion, the present invention discloses a simple and economical process for preparing vinylphenols starting from relatively cheaper and economical material 4-hydroxyphenylaldehydes and malonic acid in the presence of organic acid and organic base under microwave condition. Other objectives and advantages of the present invention will be apparent as the description progresses.

OBJECTIVES OF THE INVENTION

The main object of the present invention is to prepare high valued food flavouring substituted 4-vinylphenols from 4-hydroxyphenylaldehydes.

Yet another object of the present invention is to employ eco-friendly microwave technique for the preparation of substituted 4-vinylphenols.

Still another object of the invention is much shorter reaction time in minutes than hours required in conventional method.

Yet another object of the invention is to develop a process to prepare substituted 4-vinylphenols in good yield.

Yet another object of the invention is to develop a simple process for the preparation of substituted 4-vinylphenols in high purity with minimum side products such as cinnamic acid and polymerized product.

Yet another object of the present invention is to develop a microwave-assisted process for the preparation of substituted 4-vinylphenols where both condensation and decarboxylation occurred in one step while two individual steps are required in conventional methods.

Yet another object of the present invention is to develop a microwave-assisted process for the preparation of substituted 4-vinylphenols, which occurred in one step without any addition of decarboxylating agent, which is essential in conventional methods.

Yet another object of the invention is to develop a process to prepare substituted 4-vinylphenols in one pot.

Yet another object of the invention is to develop a process in which the acid is selected from a group of organic acids consisting of formic acid, acetic acid, propionic acid and others.

Yet another object of the invention is to develop a process in which some of condensing organic acids and organic bases such as piperidine and acetic acid are approved FEMA GRAS, which makes our process even safer and eco-friendly.

Still another object of the invention is to develop a process in which the mole ratio of the reactant to the organic base is ranging from 1:1 to 1:20.

Still another object of the invention is to develop a process in which the mole ratio of the reactant to the organic acid is ranging from 1:1 to 1:20.

Yet another object of the invention is to develop a process wherein the solvent used is selected from a group of organic acids or organic base in such a manner that it acts dual role as a solvent as well as a reagent.

Yet another object of the invention is to develop a process for easy workup as well as purification of the product.

Yet another object of the invention is to develop a process where vinylphenols are obtained by elongation of chain from C6–C1 (i.e.phenylaldehydes) to C6–C2 (i.e. vinylphenols via intermediate decarboxylation) while vinylphenols are generally obtained by shortening of the chain from C6–C3 (cinnamic acid) to C6–C2 (vinylphenols) in conventional and biotransformation methods.

Yet another object of the invention is to develop a process where the microwave induced method is also efficient and rapid to prepare not only vinylphenol (hydroxy styrene) from 4-hydroxyphenylaldehydes but also styrene from phenylaldehydes other than 4-hydroxyphenylaldehydes.

Still another object of the invention is to develop a process which utilizes less or non-hazardous chemicals.

Still another object of the invention is to develop a process, which requires cheaper chemical reagents.

Yet another object of the invention is to develop industrially viable process towards formation of high valued substituted 4-vinylphenols.

Yet another object of the invention is to develop economical process towards formation of high valued substituted 4-vinylphenols.

SUMMARY OF THE INVENTION

Accordingly, the present invention provides a process for the preparation of commercially important perfumery and food flavouring substituted 4-vinylphenols (i.e. hydroxystyrenes) such as 4-vinylguaiacol, 4-vinylphenol, 2,6-dimethoxy-4-vinylphenol. 2-hydroxy-4-vinylphenol, 3-hydroxy-4-vinylphenol and many others in one pot under microwave irradiation utilizing cheaper substrates in the form of malonic acid and substituted phenylaldehydes. The regents used are in the form of a base selected from a group of organic bases consisting of pyridine, piperidine, collidine, triethylamine and an acid selected from a group of organic acids consisting of formic acid, acetic acid, propionic acid and others. The final product i.e. substituted 4-vinylphenols was obtained in moderate yield varying from 37–51% within 20 minutes. It is worthwhile to mention that this microwave-assisted unique process is in fact an unexpected result of two individual steps (i.e. condensation and decarboxylation) observed for the first time during reaction of substituted 4-hydroxyphenylaldehydes with malonic acid in one step without addition of decarboxylating agent. In addition to above, it is also noticed that presence of hydroxy substitution at 4 position of phenylaldehyde is an essential requirement towards formation of vinylphenol in one step under microwave condition. It is also important to note that conducting the above reaction by conventional method instead of microwave provides only cinnamic acid even when substituted 4-hydroxy phenylaldehydes is taken as a starting materials.

BRIEF DESCRIPTION OF THE ACCOMPANYING DRAWINGS

DETAILED DESCRIPTION OF THE INVENTION

Figure 1:
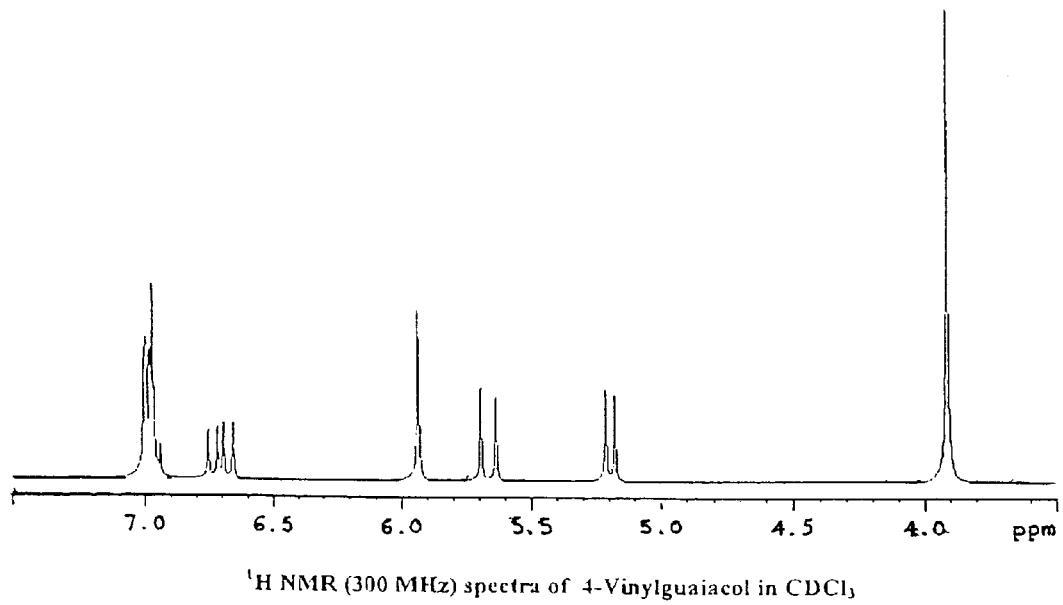
FIG. 1 is $^1$H NMR (300 MHz) spectra of vinylguaiacol (4-hydroxy-3-methoxy styrene) (in $CDCl_3$) as mentioned in Example I.
Figure 2:
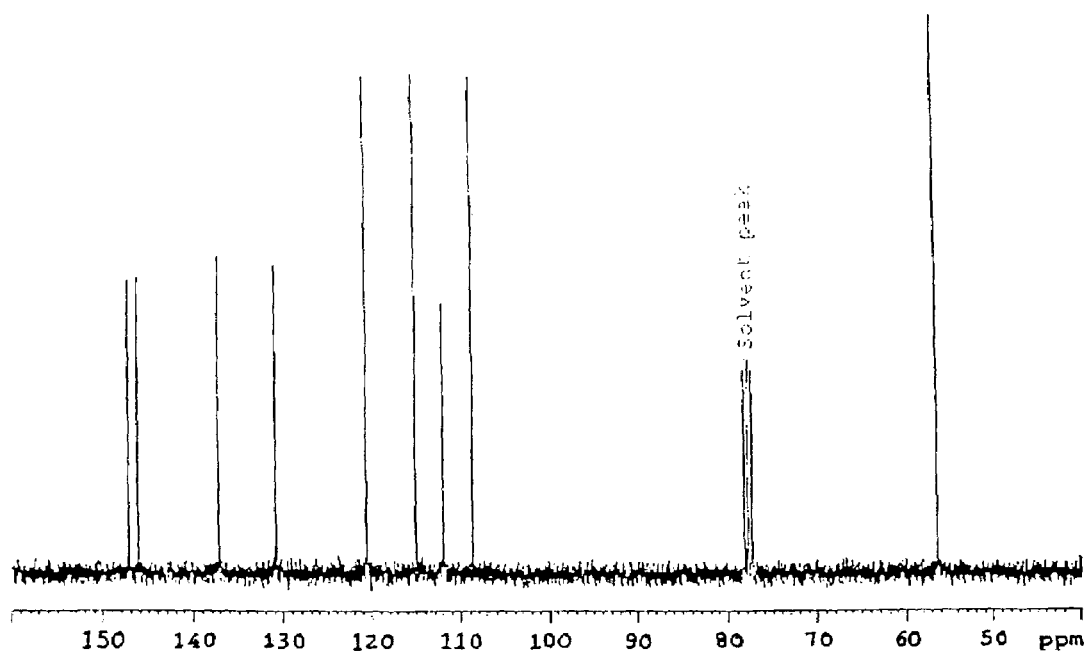
FIG. 2 is $^{13}$C NMR (75.4 MHz) spectra of vinylguaiacol (4-hydroxy-3-methoxy styrene) (in $CDCl_3$) as mentioned in Example I
Figure 3:
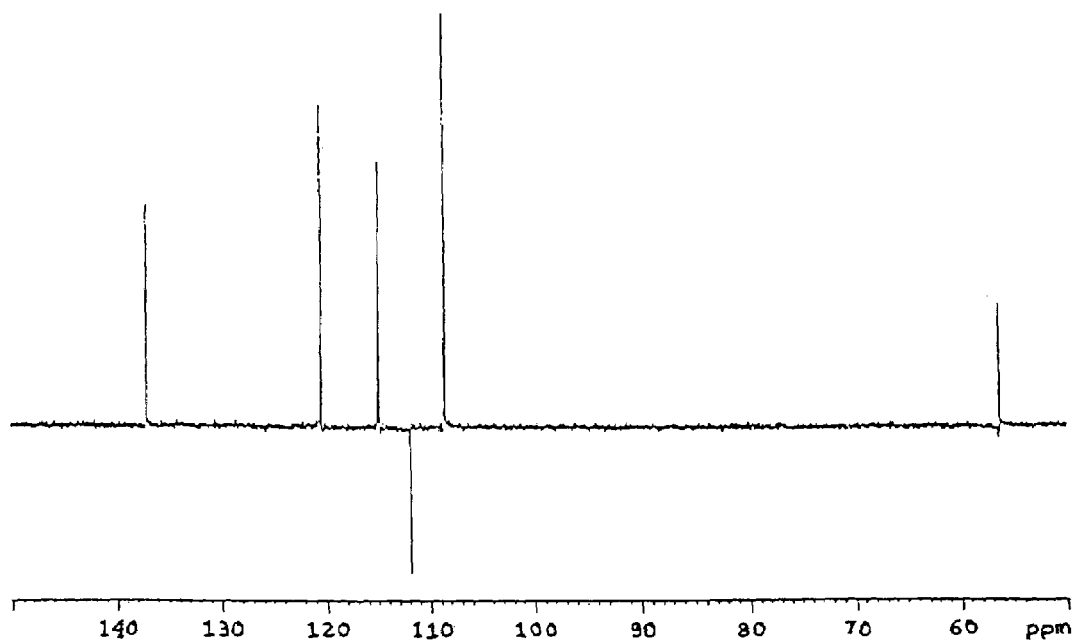
FIG. 3 is DEPT-135 NMR spectra of vinylguaiacol (4-hydroxy-3-methoxy styrene) (in $CDCl_3$) as mentioned in Example I

Accordingly, the present invention provides a microwave assisted single pot process for the preparation of 4-vinylphenol or its derivatives of general formula (I)

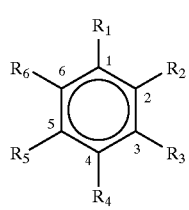

Formula I

Wherein $R_1$=OH or $OCH_3$, $R_4$=—CH—$CH_2$ and rest $R_2$, $R_3$, $R_5$ and $R_6$=H, OH or $OCH_3$ or combinations thereof, the said process comprising steps of:
a. reacting 4-hydroxyphenylaldehydes or its derivatives with malonic acid in presence of an organic base and an organic acid under microwave irradiation for a period ranging between 1 and 20 minutes,
b. cooling the mixture, pouring the cooled mixture into ice-cold water, extracting with an organic solvent, separating the organic layer,
c. washing the organic layer of step (b) with dilute hydrochloric acid followed by saturated sodium chloride solution, drying the washed organic layer over anhydrous sodium sulphate, filtering and evaporating the organic layer under reduced pressure to obtain a liquid residue,
d. purifying the liquid residue of step (c) over silica gel column, eluting with a mixture of hexane ethyl acetate, and
e. obtaining the required 4-hydroxyvinylphenols or its derivative of formula (1).

One embodiment of the present invention provides a process, wherein the organic base used the step (a) is selected from a group consisting of pyridine, piperidine, collidine, triethylamine and/or mixtures thereof.

Another embodiment, the organic acid used in step (a) selected from a group consisting of formic acid, acetic acid, propionic acid and/or mixtures thereof.

Still another embodiment, the ratio of 4-hydroxy-phenylaldehydes or its derivative and malonic acid used ranges between 1:1 and 1:3.

Yet another embodiment, the ratio of 4-hydroxyphenylaldehydes or its derivatives and organic acid, used ranges between 1:1 and 1:20.

Yet, another embodiment provides a process, wherein in step (a) the ratio of 4-hydroxyphenylaldehydes or its derivatives and organic base used ranges between 1:1 and 1:20.

In yet another embodiment, the ratio of 4-hydroxyphenylaldehydes or its derivative and organic base is in the range of 1:10.

In another embodiment of the present invention, the reaction takes place in shortest reaction time ranging from 1 to 20 minutes preferably 1–6 minutes which is remarkable reduction in the reaction time than the conventional as well as biotransformation process.

In yet another embodiment, in step (a), the reaction is taking for a period ranging between 1 and 6 minutes.

In yet another embodiment, the organic solvent used in step (b) is selected from a group consisting of toluene, dichloromethane, chloroform and ethylacetate.

In yet another embodiment, the condensation and decarboxylation is performed in a single step.

Yet another embodiment, the decarboxylation is performed without adding any decarboxylation agent.

Yet another embodiment, the said organic acid used in step (a), also acts as a solvent in addition to a reagent.

One more embodiment, the frequency of microwave irradiation ranges from 2000 to 2450 HMz.

Another embodiment, the yield of compound of formula (1) is in the range of 35% to 55%.

In another embodiment of the invention relates to a process of preparing substituted cinnamic acid derivative, wherein the said method is efficient in the preparation of substituted cinnamic acid derivative in a yield ranging between 72 to 88%.

Yet another embodiment, 4-vinylphenols or its derivatives are obtained by elongation of aldehyde carbon of 4-hydorxyphenyl aldehyde or its derivative.

In another embodiment, the invention provides easily purification of the required product and the process is eco-friendly.

In yet another embodiment of the present invention, provides substituted 4 vinylphenols in high purity with no or minimum side products.

In yet another embodiment of the present invention, provides ecofriendly and economical industrial process for the preparation of substituted 4-vinylphenols in good yield.

In yet another embodiment of the present invention, provides a unique process where 4-vinylphenols are obtained via elongation of chain from C6–C1 (phenylaldehydes) to C6–C2 (vinylphenols) whereas conventional and microbial transformation discloses the formation of vinylphenols via shortening of chain from C6–C3 (cinnamic acids) to C6–C2 (vinylphenols).

Flavour and fragrance chemistry represent one of the important branches of natural product which is in great demand for food, perfumery, and pharmaceutical industries. Several methods including chemical synthesis, biotechnology and natural extraction are being carried out by the scientific community for the smooth production of aroma chemicals. Some of vinylphenols and related styrenes are widely used in fragrances and flavours as safe aroma molecules for human consumption, though, high concentration of vinylphenols sometimes produce an off-note in flavours. Beside, vinylphenols are also known to possess a wide range of biological activities including antibacterial, antifungal and hypolipidemic activities etc. (William, A. A., David, J. M. and Priyotosh, C., Phytochemistry, 42(5), 1321–1324 (1996); Adriana, C., Leticia, G., Maria, S., Elizdath, M., Hugo, A. J., Francisco, D., Germán, C. and Joaquín, T., Arzneim.-Forsch./Drug Res., 51(II), 535–544 (2001)). In addition to above, vinylphenols and related styrenes are also found as versatile intermediates for a wide range of products (Stuart, R. R., Colette, S. M. and David, J. L., Biorganic & Medicinal Chemistry, 2(6), 553–556 (1994); Atsushi, M., Takeo, K. and Yoshinobu, I., Reactive & Functional Polymers, 37, 39–47, (1998); Michel, C. B., Adriano, L. M. and Igor, T., J. of Molecular Catalyst A: Chemical, 143, 131–136 (1999) and Pedro. J. C., Bárbara, G. and Miguel, A. R., Tetrahedron Letters, 41, 979–982 (2000).

The widespread natural vinylphenols and related styrenes are obtained from a variety of plants e.g. 2-methoxy-4-vinylphenol, also known as vinylguaiacol (FEMA GRAS NO. 2675) is obtained from the pods of *Hibiscus esculentus* (okra) and *Digitaria exilis* and also found in cooked apple, grapefruit juice (*Citrus paradisi*), feijoa fruit (*Feijoa sellowiana*), *Vitis vinifera*, strawberry fruit, raw asparagus, leaves and stalks of celery, crispbread, white wine, red wine, coffee, partially fermented tea, roasted peanuts (*Arachis hypogea*), raw beans, red sage (*Taxus sage*) and other natural sources (Jennifer, M. A. and Glesni, M., Phytochemistry, 29 (4), 1201–1207 (1990); Hanna, P., Michael, N., Uri, Z., Russell, L. R. and Steven, N., J. Agric. Food Chem., 40, 764–767 (1992) and Lasekan, O. O., Teixeira, J. P. F. and Salva, T. J. G., Food Chemistry, 75, 333–337 (2001)). In addition to above, 4-vinylguiacol is also present in several coffee plants wherein out of more than 100 different chemical constituents, 4-vinylguiacol is identified as one of the most powerful potent odorants on the basis of aroma extract dilution analysis (AEDA) (Flavour Science Recent Developments, ed. Taylor, A. J. and Mottram, D. S., The Royal Society of Chemistry, pp.200–205 (1996)). Similarly, 4-vinylguiacol is also found as one of the most odour active compounds in roasted white sesame seeds which are widely used as a flavouring material in food stuffs. In Asia, the oil isolated from the roasted sesame seed is used in seasoning of many dishes, while in Europe and United States, the roasted seeds are used in bakery products (Progress In Flavour Precursor Studies, ed. Schreier, P., Winterhalter, P., Allured Publishing Corporation, USA, 343–360 (1993) and Toshiro, W., Akira, Y., Shiro, N. and Shigero, T., J. of Chromatography A, 793, 409–413 (1998)). On the same lines, 4-vinylphenol, also known as 4-hydroxystyrene, (FEMA GRAS NO. 3739) is found in cooked apple, black currants (buds), raw asparagus, tomato, cognac, white wine, red wine, rose wine, coffee, green tea, partially fermented tea, microbial fermented tea, heated soyabean, *Boletus edulis*, coriander seed (*Coriandrum sativum*), oil of vetiver (*Vetiveria zizamioides*), olive oil and other natural sources (Souleymane, S. and Jean C., Phytochemistry, 12, 2925–2930, (1973); Takayuki, S. and Osamu, N., Phytochemistry, 21(3), 793, (1982); Makoto, O., Kazumasa, W., Haruki, N. and Kiyoyuki, Y., Tetrahedron, 43(22), 5275–5280, (1987); Saez, J. J. S., Garraleta, M. D. H. and Otero, T. B., Analytica Chimica Acta, 247(2), 295–297, (1991); Vicente, F., Ricardo, L., Ana, E. and Juan, F. C., J. of Chromatography A, 806 349–354, (1998); Nicholas, J. W., Arjan, N., Craig, B. F. and Gray, W., Current Opinion in Biotechnology, 11, 490–496 (2000); Rainer, P., Alexander, S. and Horst, P., FEMS Microbiology Letters, 205, 9–16 (2001); Ricardo, L., Margarita, A., Juan, C. and Vicente, F., J. of Chromatography A, 966, 167–177 (2002); Kuroda, K. and Dimmel, D. R., J. of Analytical and Applied Pyrolysis, 62, 259–271 (2002); Kuroda, K., Izumi, A., Mazumder, B. B., Ohtani, Y. and Sameshima, K., J. of Analytical and Applied Pyrolysis, 64, 453–463 (2002) and Daniel, F., Ivano, V. and Colin, E. S., J. of Chromatography A, 967, 235–242 (2002)). Apart from the above-mentioned vinylphenols, there are several other styrenes, which are found in different plants and are known for various applications. For example, styrene, also known as ethylene benzene (FEMA GRAS NO. 3233), is found in *Psidium guajava* (guava fruit), *Annus comosus* (pineapple), *Arachis hypogea* (roasted peanuts) and also in dairy and beverage products. Similarly, o-vinylanisole (FEMA GRAS No. 3248) is found in *Origanum vulgare*, whereas, 4-vinylveratrole and 2,4,5-trimethoxy-1-vinylbenzene are found in rum, coffee and in several other natural products (Nagashima, F., Murakami, Y. and Asakawa, Y., Phytochemistry, 51, 1101–1104 (1999).

In the pretext of above discussion, 4-vinylphenols and related styrenes can unhesitatingly be counted as greatly valued to humankind. However, the limited percentage of these substituted 4-vinylphenols in plant kingdom is not sufficient to fulfill the world demand. As a result, a large quantity of 4-vinylphenols and related styrenes are made synthetically as well as through microbial transformation where the production of styrenes from cinnamic acid has been the most extensively investigated method. A number of chemical methods are reported in literature for the preparation of vinylphenols and related styrenes (Alwyn, S., J. of Organometallic Chemistry, 247, 117–122, (1983); Matthias, B., Hartmut, F. and Klaus, K., Tertahedron Lettrs, 35(47), (1994); Cavani, F. and Trifirò, F., Applied Catalysis A: General, 133, 219–239 (1995); Atsushi, T., Atsushi, M., Takeo, K. and Yoshinobu, I., Reactive & Functional Polymers, 37, 39–47, (1998); Takaya, M., Roy, A. P., Douglas, J. T. and Hajime, Y., Journal of Catalysis, 206, 272–280 (2002)), however, the most widely used chemical methods for preparing styrenes involve decarboxylation of trans-cinnamic acids which is carried out by heating under reflux the cinnamic acids at 200–300° C. for several hours in quinoline in the presence of copper powder (Organic Synthesis Collective Volume I, 441–442 (1941) and Volume IV, 731–734 (1963); Robert, A. S., Charles, R. D. and Leo, A. P., Tertrahedron Letters, 49, 4447–4450 (1976)). Similarly, catalytic oxidation of 1,1-diphenylethane (1,1-di-(4-hydroxyphenyl)ethane) provides styrene (i.e. 4-hydroxy-3-methoxystyrene) (Perfume and Flavor Chemicals (Aroma Chemicals), ed. Steffen, A., Allured Publishing Corporation, Vol II, 1891 (1994)). In addition to chemical methods, several microbial transformations are also reported for the preparation of styrenes especially substituted vinylphenols (Masumi. T. and Kazuo, A., Tetrahedron Letters, 40, 6595–6598 (1999) and Encyclopedia of Food and Color Additives, ed. George, A. B., CRC Press, Inc., Vol II, 1705 (1996)). So far, the published biotransformation including patent processes for the production of styrenes provide relatively low yields since vinylphenols and related styrenes get further degraded to other side products e.g. biotransformation of ferulic acid provides not only the main product 4-vinylguaiacol but also vanillin, vanillic acid and protocatechuic acid as side products, depending upon biocatalyst and conditions (Takuya, K., Yasurou, I., Shinji, F., Kiyoshi, I. and Kimlo, I, J. of Fermentation and Engineering, 82(1), 46–50, (1996); Lee, I, Volm, T. G. and Rosazza, J. P. N., Enzyme and Microbial Technology. 23, 261–266, (1998)). Some other fermentation processes are also known in which ferulic acid is decarboxylated to 4-vinylguaiacol. A well-known example is the production of wheat beer where a specific top-yeast produces 4-vinylguiacol from ferulic acid in high concentration. This high concentration of 4-vinylguiacol imparts a characteristic flavour to the beer and greatly adds to its value (Understanding Natural Flavours, ed Pigget, J. R. and Patterson, A., Blackie Academic & Professional, New York, pp.211–227 (1994)). Similarly, several other microorganisms, fungi, yeast and bacteria are able to decarboxylate a large number of substituted cinnamic acids into corresponding substituted styrenes including vinylphenols from hydroxycinnamic acids Yasuyuki, H. and Santoshi, T., Archives of Biochemistry and Biophysics, 359(2), 225–230, (1998); Edlin, D. A. N., Narbad, A., Gasson, M. J., Dickinson, J. R. and Lloyd, D., Enzyme and Microbial Technology, 22, 232–239 (1998); Masumi, T. and Kazuo, A., Tetrahedron Lettrs, 40, 6595–6598, (1999); Tripathi, U, Rao, S. R. and Ravishankar, G. A., Process Biochemistry, 38, 419–426, (2002)).

All the above methods have various limitations, for example, low yield, expensive reagents and formation of unwanted side products. Keeping in view the above problems, we disclose a unique and novel microwave-assisted process to prepare 4-vinylphenols and related styrenes (Examples I, II, III) in one step from hydroxy substituted phenylaldehydes and malonic acid in the presence of an organic base and an organic acid (Jean, J. V. E. and Delphine, R., Tetrahedron, 55, 2687–2694 (1999)). In fact, it is a chance observation in which we were trying to emulate Knoevenagel Doebner condensation (Furniss, B. S., Hannaford, A. J., Rogers, V., Smith, P. W. G. and Tatchell, A. R: In: Vogel's Textbook of Practical Organic Chemistry. fourth Edn. (ELBS, UK), 802 (1978)) reaction under microwave irradiation because of advantages inherent with microwave especially shorter reaction time, minimum or no side products, and overall environmental friendly conditions (Bose, A. K., Banik, B. K., Lavlinskaia, N., Jayaraman, M. and Manhas, M. S., Chemtech, 27, 18–24, (1997); Larhed, M. and Hallberg, Drug Discovery Today, 6(8), 406–416, (2001); Kuang, C., Senboku, H. and Tokuda, M., Tetrahedron, 58, 1491–1496, (2002) and Kuhnert, N., Angew. Chem. Int. Ed., 41, 1863–1866, (2002)). With this intention, microwave assisted condensation of 3,4,5-trimethoxybenzaldehyde and malonic acid was performed towards formation of 3,4,5-trimethoxycirnamic acids (Example IV) followed by its dehydrogenation to obtain a rarer natural 3-(3,4,5-trimethoxy)phenylpropionic acid (Example V) since a large number of biologically active 3-phenylpropionic acids have been found in nature and some of substituted 3-phenylpropionic acids are intermediate for synthesis of useful organic compounds as well as synthesis of various drugs such as anti-aids, nonsteroidal, anti-inflammatory drug and dopamine D3 receptor antagonist drug (Das, B.; Kashinatham, A.; Srinivas, K. V. N. S. Planta Medica, 62, 582, (1996); Johannes, G. V.; Gerarad, R.; Richard, G. Tetrahedron Letters, 39 8329–8332, (1998); Kamperdick, C.; Phuong, N. M.; Sung, T. V., Schmidt, J. Phytochemistry, 52, 1671–1676, (1999); Susanne, H. R.; Kerry, C. A.; Dac, D. M.; Duncan, J. N.; Christopher, H. L.; Rita, H. M.; Mary, L. E.; Nanette, N. F.; Martin, S. W.; Kjell, S. A.; Matt, Z. J.; Arvid, C.; Lin, C. H., J. Med. Chem., 44, 4716–4732, (2001)). With the success of the preparation of 3,4,5-trimethoxycinnamic acid and its dihydro product (3,4,5-trimethoxy dihydrocinnamic acid), a large number of other substituted benzaldehydes (i.e. 4-methoxybenzaldehyde or 3,4-dimethoxybenzaldehyde or 2,4,5-trimethoxybenzaldehyde or dioxymethylene-benzaldehyde or 3-chlorobenzaldehyde or 4-nitrobenzaldehyde etc.) were found successful under microwave towards formation of corresponding cinnamic acids (i.e. 4-methoxycinnamic acid or 3,4-dimethoxybenzaldehyde or 2,4,5-trimethoxycinnamic acid or dioxymethylene cinnamic acid or 3-chlorocinnamic acid or 4-nitrocinnamic acid etc.) including 3-hydroxycinnamic acid (Example VII). Surprisingly, microwave assisted condensation of 3-methoxy-4-hydroxybenzaldehyde (vanillin) with malonic acid failed to provide expected 3-methoxy-4-hydroxycinnamic acid (ferulic acid) but it provided a good smelling liquid compound, which is identified as 4-vinylguaiacol on the basis of spectral data (Example I). $^1$H NMR of liquid compound showed 14 protons (Example I) which is expected for protons of ferulic acid (Example VI), however, we found two different dolublet at $\delta$ 5.19 (1H, d), and $\delta$ 5.66 (1H, d), besides a double of doublet at $\delta$ 6.6 (2H, dd), which was unlike ferulic acid where two doublets appear at $\delta$ 5.7 (1H, d), and at $\delta$ 6.7 (1H, d). Similarly, $^{13}$C NMR of liquid compound indicates the presence of 9 carbons (Example I) without presence of carbonyl group instead of 10 carbons including carbonyl group as expected for ferulic acid. DEPT-135 confirms the presence of one $CH_2$ at $\delta_c$ 111.8. Overall spectral data indicates the presence of 4-vinylguaiacol and not the ferulic acid as expected. Finally, mass spectra confirm the structure liquid as 4-vinyl guaiacol (99.4% purity by GC).

In conclusion, our invention discloses a simple and economical process for preparing vinylphenols starting from relatively cheaper and economical material 4-hydroxyphenylaldehydes and malonic acid in the presence of organic acid and organic base under microwave condition, which avoids the use of cinnamic acid and decarboxylating agent and longer reaction time.

EXAMPLES

The following examples are given by way of illustration of the present invention and should not be construed to limit the scope of the present invention.

The starting material substituted phenylaldehydes including 4-hydroxy phenylaldehydes such as vanillin, 4-hydroxybenzaldehydephenylpropane derivatives or the like, can be obtained from commercial sources. Kenstar microwave oven (2450 MHz, 1200 Watts) is used for all the given reactions.

Example I

Synthesis of 4-vinylguaiacol (by microwave irradiation method): A mixture of vanillin (2.50 g, 0.0164 mol), malonic acid (3.41 g, 0.0328 mol), piperidine (3–5 ml) and acetic acid (10–20 mL) were taken in a 100 ml Erlenmeyer flask fitted with a loose funnel at the top. The flask was shaken well and placed inside the microwave oven and irradiated for 1–7 minutes in parts. The cooled mixture was poured into ice-cold water and extracted with ethyl acetate. The organic layer was washed with dil HCl., saturated sodium chloride and then organic layer dried over sodium sulphate. The solvent was evaporated under reduced pressure to obtain liquid which was purified on silica gel column chromatography using mixture of hexane and ethyl acetate (9:1 to 6:4), provided sweet and pleasant smelling liquid in 51% yield; $^1$H NMR (CDCl$_3$) δ 6.96 (3H, m, 3,5,6-Ar), 6.70 (1H, dd, J=7.8 Hz, CH=CH$_2$), 5.93 (1H, s, OH), 5.66 (1H, d, J=17.6, cis-CH=CH$_2$), 5.19 (1H, d, J=10.9 Hz, trans-CH=CH$_2$), 3.90 (3H, s, OMe); $^{13}$C NMR (CDCl$_3$) δ 147.1 (C-1), 146.07 (C-2), 137.1 (CH=CH$_2$), 130.7 (C-4), 120.4 (C-6), 114.9 (C-5), 111.8 (CH=CH$_2$), 108.5 (C-3), 56.2 (OCH3).

Example II

Synthesis of 4-vinylphenol (4-hydroxystyrene) (by microwave irradiation method): A mixture of 4-hydroxybenzaldehyde (1.0 g, 0.0082 mol), malonic acid (1.69 g, 0.0163 mol), triethylamine(2–4 mL) and acetic acid (10–15 mL) were taken in a 100 ml Erlenmeyer flask fitted with a loose funnel at the top. The flask was shaken well and placed inside the microwave oven and irradiated for 2–8 minutes in parts. The cooled mixture was poured into ice cold water and extracted with ethyl acetate. The organic layer was washed with sodium bicarbonate, dil HCl., saturated sodium chloride and then organic layer dried over sodium sulphate. The solvent was evaporated under reduced pressure to obtain liquid which was purified on silica gel column chromatography using mixture of hexane and ethyl acetate (9:1 to 6:4), provided sweet and pleasant smelling liquid in 40% yield; $^1$H NMR (CDCl$_3$) δ 7.31 (2H, d, J=8.5 Hz, H-2 and H-6), 6.81 (2H, d, J=8.8 Hz, H-3 and H-5), 6.67 (1H, dd, J=17.8 Hz, 11.3 Hz, (CH=CH$_2$), 5.51 (1H, s, OH), 5.2 (1H, d, J=17.8, cis-CH=CH$_2$), 5.14 (1H, d,J=11.3 Hz, trans-CH=CH$_2$); $^{13}$C NMR (CDCl$_3$) δ 155.5 (C-1), 136.5 (CH=CH$_2$), 130.9 (C-4), 128.0 (C-3 and C-5), 115.8 (C-2 and C-6), 112.0 (CH=CH$_2$).

Example III

Synthesis of 3,5-dimethoxy-4-vinylphenol (by microwave irradiation method): A mixture of 4-hydroxy-3,5-dimethoxy benzaldehyde (2.5 g, 0.013 mol), malonic acid (2.80 g, 0.027 mol), piperidine (2–5 mL) and formic acid (10–20 mL) were taken in a 100 ml Erlenmeyer flask fitted with a loose funnel at the top. The flask was shaken well and placed inside the microwave oven and irradiated for 2–8 minutes in parts. The cooled mixture was poured into ice cold water and extracted with ethyl acetate. The organic layer was washed with dil HCl., saturated sodium chloride and then organic layer dried over sodium sulphate. The solvent was evaporated under reduced pressure to obtain liquid which was purified on silica gel column chromatography using mixture of hexane and ethyl acetate (9:1 to 6:4), provided a viscous liquid in 37% yield; $^1$H NMR (CDCl$_3$) δ 6.73(1H, s, H-3 and H-5), 6.62 (1H, dd, CH=CH$_2$) 5.61 (1H, d, J=18.6 Hz, cis-CH=CH$_2$), 5.16(1H, d, J=10.8, trans-CH=CH$_2$); $^{13}$C NMR (CDCl$_3$) δ 147.4 (C-2) and C-6), 137.2 (C-1), 135.1 (CH=CH$_2$), 129.5 (C-4), 112.2 (CH=CH$_2$), 103.3 (C-3 and C-5), 56.0 (2-OMe).

Example IV

Synthesis of 3,4,5-trimethoxycinnamic acid (by microwave irradiation method): A mixture of 3,4,5-trimethoxybenzaldehyde (5.0 g, 0.025 mol), malonic acid (5.30 g, 0.050 mol), piperidine (4–8 mL) and acetic acid (25–35 mL) were taken in a 100 ml Erlenmeyer flask fitted with a loose funnel at the top. The flask was shaken well and placed inside a microwave oven and irradiated for 4–8 minutes in parts. The cooled mixture was poured into ice cold water and then acidified with 5% HCl. The precipitated yellow solid was filtered and recrystallized with aq. ethanol to afford 3,4,5-trimethoxycinnamic acid in 88% yield; mp 127° C. (lit mp 126–128° C.) whose spectral data was found similar to the reported values $^1$H NMR (CDCl$_3$) δ 7.73 (1H, d, J=16.0 Hz, —CH=CH—COOH), 6.78 (2H, s, H-2 & H-6), 6.38 (1H, d, J=16.0 Hz, CH=CH—COOH), 3.91 (9H, s, 3-OCH$_3$, 4-OCH$_3$ & 5-OCH$_3$); $^{13}$C NMR: δ 172.6 (COOH), 153.8 (C-3 and C-5), 147.4 (C-4), 140.8 (CH=CH—COOH), 129.8 (C-1), 116.8 (CH=CH—COOH), 105.8 (C-2 and C-6), 61.4 (4-OCH$_3$), 56.5 (3-OCH$_3$ and 5-OCH$_3$).

Example V

Synthesis of 3-(3,4,5-trimethoxy)phenylpropionic acid (by microwave irradiation method): 3,4,5-trimethoxycinnamic acid (0.72 g, 0.003 mole), PdCl$_2$ (55 mg, 0.31 mmol), 10% sodium hydroxide (6–10 mL) were suspended in a 100 ml Erlenmeyer flask and added formic acid (8–12 mL) in parts. The mixture was irradiated with microwave for 3–5 min. till disappearance of starting material. The cooled mixture was poured into ice cold water, acidified with 5% HCl and extracted with dichloromethane (3×10 mL). The organic layer was washed with water and dried over anhydrous Na$_2$SO$_4$. The solvent was evaporated and the crude solid product was recrystallized with a mixture of ethylacetate and hexane to provide 3-(3,4,5-trimethoxy)phenylpropionic acid as a white solid in 84% yield; mp 102° C. (lit mp 101–102° C.); $^1$H NMR (CDCl$_3$) δ 6.70 (2H, s,H-2 and H-6), 3.84 (9H, s, 3-OCH$_3$, 4-OCH$_3$), and 5-OCH$_3$), 2.92 (2H, t, Ar-CH$_2$—CH$_2$—COOH), 2.70 (2H, t, —CH$_2$—CH$_2$—COOH); $^{13}$C NMR: δ 178.1 (COOH), 153.1 (C-3 & C-5), 135.87 (C-4 & C-1), 105.3 (C-2 & C-6), 60.8.0 (4-OCH$_3$), 56.1 (3-OCH$_3$ & 5-OCH$_3$), 35.5 (Ar—CH$_2$—), 31.0 (—CH$_2$—COOH).

Example VI

Synthesis of ferulic acid (by conventional method): A mixture of vanillin (2.50 g, 0.0164 mol), malonic acid (3.41 g; 0.0328 mol), piperidine (3–5 mL) and acetic acid (10–20 mL) were taken in a round bottom flask and the reaction mixture was refluxed for 5–6 hours instead of microwave irradiation as mentioned in Example I. The cooled mixture was poured into ice-cold water and extracted with ethyl acetate. The organic layer was washed with dil HCl., saturated sodium chloride and then organic layer dried over sodium sulphate. The solvent was evaporated under reduced pressure to obtain solid which was recrytallised with mixture of methanol and hexane, provided ferulic acid as a solid compound mp 169° C. (lit mp 168–171° C.) in 65% yield;

$^1$H NMR (DMSO-d$_6$) δ 12.13 (1H, s, COOH), 7.48 (1H, d, Ar—$\overline{\text{CH=CH}}$—COOH), 7.27 (1H, s, H-3), 7.07 (1H, d, H-6), 6.78 (1H, d, H-5), 6.36 (1H, d, —CH=CH—COOH), 3.81 (3H, s, 2-OCH$_3$); δ168.9 (COOH), 149.8 (C-1), 148.7 (C-2), 145.4 (CH=CH—COOH), 126.6 (C-4), 123.7 (C-5), 116.4 (C-3 & C-6), 111.8 (CH=CH—COOH), 56.4 (2-OCH$_3$).

This experiment clearly indicates that utilization of microwave technique is important for the preparation of 4-vinylguaiacol from vanillin and malonic acid (Example I).

Example VII

Synthesis of 3-hydroxycinnamic acid (by microwave irradiation method): A mixture of 3-hydroxybenzaldehyde (1 g, 0.008 mol), malonic acid (1.69 g, 0.016 mol), piperidine (1 to 3 mL) and acetic acid (10–20 mL) were taken in a 100 ml Erlenmeyer flask and irradiated under microwave for 2–8 minutes in parts. The cooled mixture was poured into ice cold water and extracted with ethyl acetate. The organic layer was washed with dil HCl., saturated sodium chloride and then organic layer dried over sodium sulphate. The solvent was evaporated under reduced pressure to obtain crude solid which was recrystallised with methanol, provided a white solid in 76% yield; 193° C. (lit mp 194° C.); $^1$H NMR (CDCl$_3$) δ 6.73(1H, s, H-3 and H-5), 6.62 (1H, dd, H-7), 5.61(1H, d, J=10.9 Hz trans, H-8), 5.16(1H, d, J=17.6, cis-H-8).; $^{13}$C NMR (CDCl$_3$) δ 147.4 (C-2 and C-6), 137.2 (C-1), 135.1 (C-7), 129.5 (C-4), 112.2 (C-8), 103.3 (C-3 and C-5), 56.0 (2 OMe). This experiment clearly indicates that utilization of microwave technique as well as presence of hydroxy at 4-position of phenylaldehydes is important for the preparation of 4-vinylphenols (Example I, II and III).

The Main Advantages of the Present Invention are

The main advantage of the present invention is a process to prepare high valued food flavouring substituted 4-vinylphenols from 4-hydroxyphenylaldehydes.

A process to employ ecofriendly microwave technique for the preparation of substituted 4-vinylphenols.
1. A process to prepare 4-vinylphenols in much shorter reaction time in minutes.
2. A process to prepare substituted 4-vinylphenols in good yield (37–55%).
3. A process for the preparation of substituted 4-vinylphenols in high purity with minimum or no side products such as cinnamic acid and polymerized product.
4. A process to develop a microwave-assisted preparation of substituted 4-vinylphenols where both condensation and decarboxylation unexpectedly occurred in one-step, which otherwise requires two individual steps in conventional methods.
5. A process to prepare substituted 4-vinylphenols in one pot.
6. A process in which the base is selected from a group of organic bases consisting of pyridine, piperidine, collidine, triethylamine and others.
7. A process in which the acid is selected from a group of organic acids consisting of formic acid, acetic acid, propionic acid and others.
8. A process in which the mole ratio of the reactant to the organic base is ranging from 1:1 to 1:20.
9. A process in which the mole ratio of the reactant to the organic acid is ranging from 1:1 to 1:20.
10. A process wherein the solvent used is selected from a group of organic acids or organic base in such a manner that it plays dual role both as a solvent as well as a reagent.
11. A process for easy workup as well as purification of the product.
12. A process which utilizes less or non-hazardous chemicals.
13. A process, which requires cheaper chemical reagents.
14. A process to develop industrially viable process towards formation of high valued substituted 4-vinylphenols.
15. A process to develop economical process towards formation of high valued substituted 4-vinylphenols.

What is claimed is:

1. A microwave assisted single pot process for the preparation of 4-vinyiphenol or its derivatives of general formula (I)

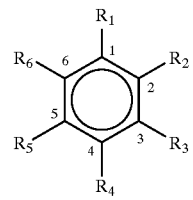

Formula I wherein R$_1$=OH or OCH$_3$, R$_4$=—CH—CH$_2$ and rest R$_2$, R$_3$, R$_5$ and R$_6$=H, OH or OCH$_3$ or combinations thereof, the said process comprising steps of:
 a. reacting 4-hydroxyphenylaldehydes or its derivatives with malonic acid in presence of an organic base and an organic acid under microwave irradiation for a period ranging between 1 and 20 minutes,
 b. cooling the mixture, pouring the cooled mixture into ice-cold water, extracting with an organic solvent, separating the organic layer,
 c. washing the organic layer of step (b) with dilute hydrochloric acid, followed by saturated sodium chloride solution, drying the washed organic layer over anhydrous sodium sulphate, filtering and evaporating the organic layer under reduced pressure to obtain a liquid residue,
 d. purifying the liquid residue of step (c) over silica gel column, eluting with a mixture of hexane ethyl acetate, and
 e. obtaining the required 4-hydroxyvinylphenols or its derivative of formula (1).

2. A process of claim 1, wherein the step (a) the organic base used is selected from a group consisting of pyridine, piperidine, collidine, triethylamine and/or mixtures thereof.

3. A process of claim 1, wherein the step (a) the organic acid used is selected from a group consisting of formic acid, acetic acid, propionic acid and/or mixtures thereof.

4. A process of claim 1, wherein in step (a) the ratio of 4-hydroxy-phenylaldehydes or its derivative and malonic acid used ranges between 1:1 and 1:3.

5. A process of claim 1, wherein in step (a) the ratio of 4-hydroxyphenylaldehydes or its derivatives and organic acid used ranges between 1:1 and 1:20.

6. A process of claim 1, wherein in step (a) the ratio of 4-hydroxyphenylaldehydes or its derivatives and organic base used ranges between 1:1 and 1:20.

7. A process of claim 6 wherein the ratio of 4-hydroxyphenylaldehydes or its derivative and organic base is in the range of 1:10.

8. A process of claim 1 wherein in step (a) the reaction time period is in the range of 1 to 6 minutes.

9. A process of claim 1, wherein the step (b) the organic solvent used is selected from a group consisting of toluene, dichloromethane, chloroform or ethylacetate.

10. A process of claim 1 wherein in step (a), the said organic acid used, also acts as a solvent in addition to a reagent.

11. A process of claim 1, wherein the frequency of microwave irradiation range from 2000 to 2450 MHz.

12. A process of claim 1 wherein the yields of compounds of formula (1) is in the range of 35% to 55%.

* * * * *